(12) United States Patent
Park et al.

(10) Patent No.: US 10,596,039 B2
(45) Date of Patent: Mar. 24, 2020

(54) MACHINE-READABLE MEDIUM, KERATOTOMY SYSTEM, AND KERATOTOMY METHOD

(71) Applicants: Jin Young Park, Toronto (CA); Jin A. Park, Toronto (CA); Ki Sung Park, Hwaseong (KR); In Kyung Park, Suwon (KR); Kee Cheol Park, Yongin (KR)

(72) Inventors: Jin Young Park, Toronto (CA); Jin A. Park, Toronto (CA); Ki Sung Park, Hwaseong (KR); In Kyung Park, Suwon (KR); Kee Cheol Park, Yongin (KR)

( * ) Notice: Subject to any disclaimer, the term of this patent is extended or adjusted under 35 U.S.C. 154(b) by 119 days.

(21) Appl. No.: 15/543,567

(22) PCT Filed: Sep. 8, 2015

(86) PCT No.: PCT/KR2015/009454
§ 371 (c)(1),
(2) Date: Jul. 13, 2017

(87) PCT Pub. No.: WO2016/153133
PCT Pub. Date: Sep. 29, 2016

(65) Prior Publication Data
US 2018/0008465 A1    Jan. 11, 2018

(30) Foreign Application Priority Data

Mar. 24, 2015  (KR) .................. 10-2015-0040859

(51) Int. Cl.
*A61F 9/008* (2006.01)
*A61B 3/10* (2006.01)

(52) U.S. Cl.
CPC ........ *A61F 9/00808* (2013.01); *A61B 3/1005* (2013.01); *A61F 9/008* (2013.01);
(Continued)

(58) Field of Classification Search
CPC .................. A61F 9/008–2009/00897; A61B 18/20–18/28; A61B 34/00–2034/108; A61B 3/1005; A61N 5/06–2005/073
(Continued)

(56) References Cited

U.S. PATENT DOCUMENTS

| | | | | |
|---|---|---|---|---|
| 6,547,393 B2 * | 4/2003 | Ruiz | ...................... | A61F 9/008 351/212 |
| 8,409,179 B2 * | 4/2013 | Bille | .................. | A61F 9/00827 128/898 |
| 2008/0249514 A1 * | 10/2008 | Hohla | ..................... | A61F 9/007 606/5 |

OTHER PUBLICATIONS

Jose Alberto Rodriguez Agudo et al., "Laser asymmetric ablation method to improve corneal shape", https://link.springer.com/article/10.1007%2Fs10103-019-02770-z.

* cited by examiner

*Primary Examiner* — Gary Jackson
*Assistant Examiner* — Jonathan Kuo
(74) *Attorney, Agent, or Firm* — Patent Office of Dr. Chung Park

(57) ABSTRACT

A corneal ablation system for correcting vision by using a laser is provided. The corneal ablation system includes: an operation device for creating an integrated corneal ablation plan for correcting a shape and a curvature error of a cornea based on corneal status data; a laser control unit for controlling a laser module according to an ablation position and an ablation shape of the cornea based on the integrated corneal ablation plan transmitted from the operation device; and the laser module for generating a laser and transmitting the laser to an optical unit under control of the laser control unit.

6 Claims, 25 Drawing Sheets

(52) U.S. Cl.
CPC ............... *A61F 2009/00842* (2013.01); *A61F 2009/00872* (2013.01); *A61F 2009/00878* (2013.01)

(58) Field of Classification Search
USPC .............................. 606/4–6, 10–12; 434/262
See application file for complete search history.

| Ablation form 1 | Ablation form 2 | Ablation form 3 |
|---|---|---|
| Corneal ablation form for relieving a curvature error | Corneal ablation form for relieving relieving a curvature error | Ablation form 3 |
| Two axially symmetric portions at left and right sides are cut in the same amount | Primary ablation for reducing the thickness deviation | Minute ablation for residual thickness deviation after the primary ablation |
| 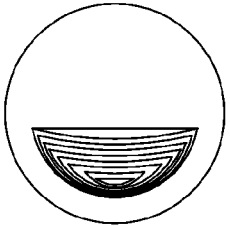 | 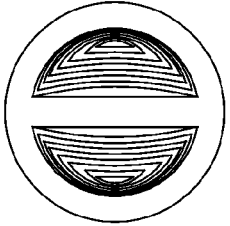 | 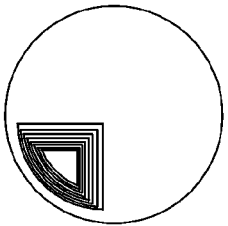 |

Fig. 18

| one semi-cylinder astigmatic ablation in one direction (1CD/1SA) | two semi-cylinder astigmatic ablations in two directions (2CD/2SA) | three semi-cylinder astigmatic ablations in three directions (3CD/3SA) |
|---|---|---|
| Correct astigmatism by removing thickness deviation through cutting only one thick portion. | No astigmatism occurs when two portions are vertically overlapped and cut in the same amount. | No astigmatism occurs when a central main ablation amount is the same as the sum of ablation amounts of two left and right portions. |

Fig. 19

| Partial corneal ablation for preventing the corneal protrusion | | Minute thickness deviation ablation |
|---|---|---|
| three semi-cylinder astigmatic ablations in three directions (3CD/3SA) | four semi-cylinder astigmatic ablations in four directions (4CD/4SA) | one quarter cylinder astigmatic ablation in one direction (1CD/1QA) |
| 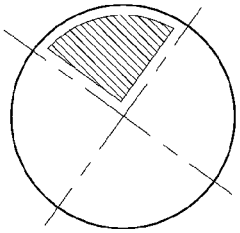 | 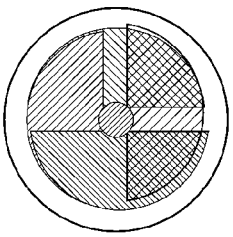 | |
| Ablation is performed for dispersing the intraocular pressure regardless of curvature fluctuation and astigmatism occurrence | | Residual thickness deviation after the semi(1/2)-cylinder astigmatic ablation is relieved |

Fig. 21

| Remarks | Conventional astigmatic correction corneal ablation method | Astigmatic correction corneal ablation method according to the present invention |
|---|---|---|
| During correction | (Right side is thicker than left side)<br><br>Cut both sides | (Right side is thicker than left side)<br><br>Cut only the thick portion |
| After correction | (Left and right thicknesses are the same) | (Left and right thicknesses are the same) |
| Result | On the thinned corneal region, the protrusion occurs due to the intraocular pressure, which changes the corneal curvature, and the path of light deviates from the visual axis. | Thickness deviation in the peripheral portion is reduced, the central portion is thinned, which concentrates the intraocular pressure on the central portion of the cornea, while locating the posterior corneal cone in the central portion of the cornea. The path of light coming from the fixation point matches the visual axis. |

Fig. 23

| Ex) +2 D corneal ablation method | | |
|---|---|---|
| Conventional curvature correction corneal ablation method | | Shape correction corneal ablation method |
| Basic corneal ablation method of cutting astigmatic-axial symmetric portions in the same curvature | Advanced corneal ablation method with customized ablation according to the curvature error in respective regions of the cornea | Corneal ablation method for correcting the shape by reducing the thickness deviation of the symmetric portions regardless of the curvature of the cornea |
| *Corneal curvature before ablation* 38D / 40D / +2D / Ablation amount / +2D | *Corneal curvature before ablation* 38D / 40D / +4D / Ablation amount / 0 | *Corneal curvature before ablation* 38D / 40D / +4D / Ablation amount / 0 |
| Thickness deviation before and after ablation is the same | After ablation, the intraocular pressure is concentrated on the thin region, so that the curvature deviation is increased again | Curvature deviation of the symmetric portions is reduced by the intraocular pressure after ablation, and the corneal protrusion is relieved |

| Low-order aberration (curvature error) and visual acuity measured before vision correction | Corneal topography showing a preoperative corneal curvature distribution map |
|---|---|
| Sph +1.0D Cyl. -0.5D Axis 180(S.E.= +0.75D)Unaided visual acuity, distance vision : 0.9 Near vision : 0.3 | |

| Low-order aberration (curvature error) measured before the surgery | Simulation of a conventional corneal ablation form for low-order aberration |
|---|---|
| Input the low-order aberration measured before corneal curvature correction plan surgery into laser, and proceed corneal ablationSph. +1.0D Cyl. -0.5D Axis 180 | |

MACHINE-READABLE MEDIUM, KERATOTOMY SYSTEM, AND KERATOTOMY METHOD

BACKGROUND OF THE INVENTION

1. Field of the Invention

The present invention relates to a system for correcting vision by using a laser and a method thereof. More particularly, the present invention relates to an integrated corneal ablation system for correcting both shape and curvature of a cornea by creating a defective shape correction scheme of correcting a defective shape of an asymmetric cornea into a symmetric cornea that has a posterior corneal cone located at a central portion of the cornea through reducing thickness deviation in view of point symmetry to relieve eccentricity of the posterior corneal cone, and combining the defective shape correction scheme with a conventional vision correction scheme of removing a low-order aberration, and a method thereof.

2. Description of the Related Art

A laser vision correction technique is known as a conventional vision correction scheme for improving the visual acuity by cutting the cornea to remove its low-order aberration.

The laser vision correction technique is a scheme of setting all corneas as an ellipse, having a spherical or axial-symmetric shape, and cutting the cornea in order to eliminate the low order aberration (spherical aberration and astigmatism).

In addition, there is a scheme of measuring the focus dispersion due to shape distortion by a corneal topography or a fractography (front wave) tester, and cutting the cornea in a customized manner corresponding to a curvature error which is mutually different according to parts of the cornea. However, both schemes are schemes that remove only the measured curvature error while ignoring the imbalance of the intraocular pressure due to the thickness deviation to correct vision. Therefore, in the case of asymmetric corneas, it is impossible for both schemes to solve intricate problems such as corneal shape distortion and vision deterioration generated by the protrusion in a peripheral part of a posterior cornea due to the intraocular pressure after the corneal ablation for vision correction has been performed.

SUMMARY OF THE INVENTION

The present invention performs integrated corneal correction to correct a defective shape of a cornea in combination with conventional low-order aberration correction. In addition, clear visual acuity is obtained through the corneal ablation method capable of improving both focal direction error and focal distance error. In this manner, there is proposed a corneal ablation method without shape distortion due to the intraocular pressure, and vision deterioration due to shape distortion after vision correction.

A machine-readable medium according to the present invention stores a program which is used to create a plan for cutting a cornea and executed by at least one operation device or operation unit, wherein the program creates an integrated corneal ablation plan for correcting both the defective shape and a curvature error by collecting corneal status information including the curvature error (low-order aberration) of the cornea, a corneal thickness distribution map, and a posterior corneal shape map, and wherein the integrated corneal ablation plan makes the cornea as a symmetric cornea that has a posterior corneal cone located at a central portion of the cornea by concentrating the intraocular pressure at a central portion of the cornea, by correcting a shape of an asymmetric cornea having an eccentric posterior corneal cone through the corneal thickness distribution map and a posterior corneal shape without fluctuation in an average corneal curvature value, and includes an ablation plan for correcting the curvature error through the low-order aberration.

A corneal ablation system according to the present invention includes: an operation device for creating an integrated corneal ablation plan for correcting the shape and curvature error of a cornea based on the data regarding the corneal status; a laser control unit for controlling a laser module according to an ablation position and an ablation shape of the cornea based on the integrated corneal ablation plan transmitted from the operation device; and the laser module for generating a laser and transmitting the laser to an optical unit under the control of the laser control unit, wherein the operation device uses information on a low-order aberration (curvature error) of the cornea, a corneal thickness distribution map, and a posterior corneal shape map—detects a position of an eccentric posterior corneal cone by using the posterior corneal shape map, obtains thickness deviation through the corneal thickness distribution map with respect to the cornea except for the position of the eccentric posterior corneal cone, eliminates the eccentric posterior corneal cone by partially cutting the cornea so as to maximally reduce the thickness deviation in view of point symmetry, and offsets corneal curvature fluctuation generated during the partial cutting by calculating a myopic spherical aberration and performing corneal ablation, which concentrates the intraocular pressure at a central portion of the cornea that is thinned after the corneal ablation. As a result, defective shape correction is completed by determining partial corneal ablation shape and amount so as to make the cornea as a symmetric cornea formed at a central portion thereof with a posterior corneal cone, and integrated corneal ablation where the defective shape and the curvature error are collectively corrected is completed by summing up corneal ablation shape and amount for conventional low-order aberration correction.

A corneal ablation method according to the present invention includes: collecting the status information on an ablation target cornea; creating a partial corneal ablation plan for reducing thickness deviation of the cornea in view of point symmetry to relieve a distortion region, based on the collected status information; creating corneal ablation plan for myopic correction by calculating a spherical aberration for offsetting curvature fluctuation generated when cutting the cornea according to the partial corneal ablation plan; calculating an interlocking low-order aberration that is to be combined with the created partial corneal ablation plan by summing up the created myopic correction corneal ablation plan with a collected low-order aberration; creating an integrated corneal ablation plan by combining the interlocking low-order aberration with the partial corneal ablation plan; and cutting the cornea by using a laser according to the integrated corneal ablation plan.

According to the corneal ablation system for integrally correcting the defective shape and the curvature error as proposed above, the asymmetric cornea that has the eccentric posterior corneal cone can be maximally reduced in the thickness deviation in view of point symmetry. In addition, a shape of the cornea can be corrected into a symmetric cornea that has the posterior corneal cone at the central portion of the cornea, and the shape distortion of the posterior cornea can be relieved by dispersing the intraocular pressure that has been concentrated in the eccentric posterior corneal cone. Further, the integrated corneal correction is performed by combining the shape correction as described above with the existing low-order aberration correction, so that both the focal direction error and the focal distance error can be improved. Thus, the curvature error and visual axis deviation of light progressing from a fixation point toward the retina is simultaneously relieved, thereby providing clear visual acuity without glare symptoms and image distortion.

In addition, problems such as shape distortion of the cornea due to the intraocular pressure that incurred after vision correction, when the asymmetric cornea that has the eccentric posterior corneal cone, is cut using the conventional vision correction scheme and vision deterioration generated due to the shape distortion can be prevented in advance.

BRIEF DESCRIPTION OF THE DRAWINGS

FIGS. 15 to 33 are views for explaining the present embodiment.

DETAILED DESCRIPTION OF THE INVENTION

Hereinafter, embodiments of the present invention will be described in detail with reference to the accompanying drawings and reference drawings.

Figure 1:
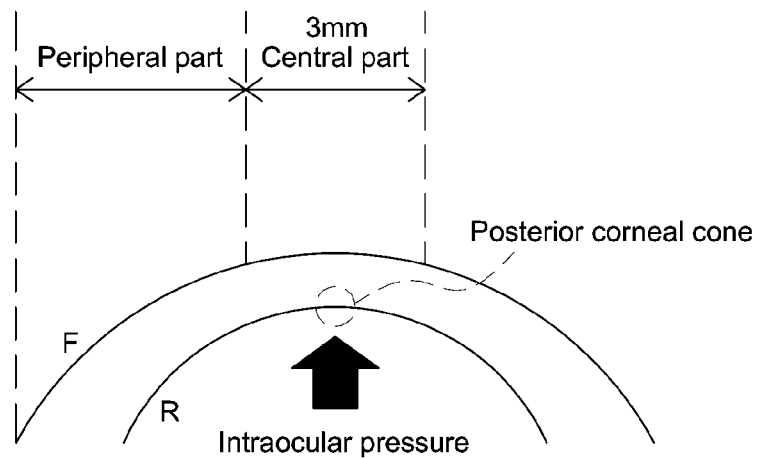
FIG. 1 is a view showing a sectional shape of a cornea without distortion.

FIG. 1 is a view showing a sectional shape of a cornea without distortion.

Referring to FIG. 1, in the case of a cornea having an ideal shape where the intraocular pressure is concentrated in a central portion of the cornea, the thickness of the cornea at its periphery part is larger than the thickness of the cornea at the central portion, and the thickness deviation in the concentric circle is minimized.

However, in the case of a cornea in which the thickness deviation significantly varies depending on the different positions in the cornea, or in which the intraocular pressure is not concentrated at the central portion of the cornea, focus deviation such as irregular astigmatism occurs, and image distortion occurs, which eventually results in vision deterioration.

As described above, the following description will be described with reference to cases in which the focus deviation is incurred.

Excellent visual acuity can be achieved in the absence of the focus deviation. The focus deviation may be classified into a focal distance error and a focal direction error (i.e., focus dispersion).

The focal distance error is caused by a curvature error of the cornea. The curvature error refers to a spherical aberration and astigmatism, which are numerical indexes representing a low-order aberration. In addition, the spherical aberration represents a curvature error of a point-symmetric cornea, and astigmatism represents a curvature error of an axial-symmetric cornea. A conventional laser corneal ablation method described above uses an ablation method as shown in FIG. 2 to correct the curvature error of myopia and hyperopia, which are point-symmetric corneas, and the curvature error of astigmatism, which is an axial-symmetric cornea.

Figure 2:
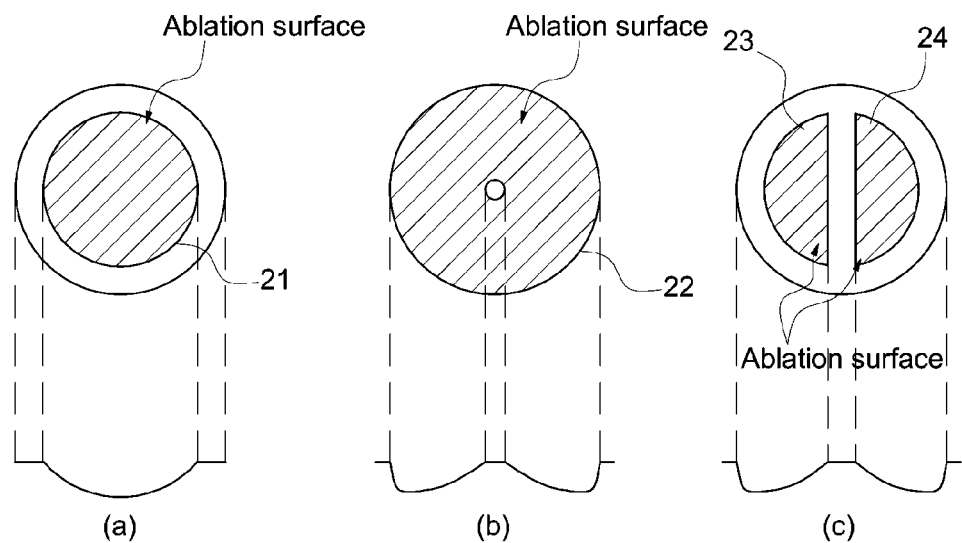
FIG. 2 is a view for explaining an existing corneal ablation method for correcting low-order aberration with a laser.

FIG. 2 is a view for explaining an existing corneal ablation method for correcting a low-order aberration with a laser. FIGS. 2(a) and 2(b) are views showing a corneal ablation method with respect to the spherical aberration incurred in a point-symmetric corneal shape in the case of myopic correction and hyperopic correction, respectively. FIG. 2(c) is a view showing a corneal ablation method with respect to an axial-symmetric corneal shape in the case of astigmatic correction.

In detail, FIG. 2(a) shows a case, for the myopic correction, where a region which has a corneal diameter of about 8.5 mm is cut through a concentric circle such that the cutting depth is gradually deepened from the peripheral part of the cornea toward the central portion 21 of the cornea.

In addition, FIG. 2(b) shows a case, for the hyperopic correction, where ablation is performed from the central portion of the cornea toward a peripheral part 22 of the cornea in a concentric circle, and the ablation depth is gradually reduced from a periphery having a diameter of about 6.5 mm toward the peripheral part having a diameter of about 8.5 mm.

Further, FIG. 2(c) shows a case where astigmatism occurs. In the case that the cornea has the axial-symmetric corneal shape, for the astigmatic correction, symmetric portions 23 and 24 of the cornea, which are symmetrical to each other about an astigmatic axis, are cut from an edge to a center of a semicircular shape obtained by dividing the diameter of 8.5 mm by half.

On the other hand, the focal direction error refers to the generation of a high-order aberration such as a coma aberration caused by the focus deviation due to a defective shape of the cornea. The defective shape of the cornea is a distortion phenomenon occurring in a mid-peripheral part and a peripheral part of a posterior cornea caused by the unbalance of the intraocular pressure due to the thickness deviation, resulting in an asymmetric cornea.

Figure 3:
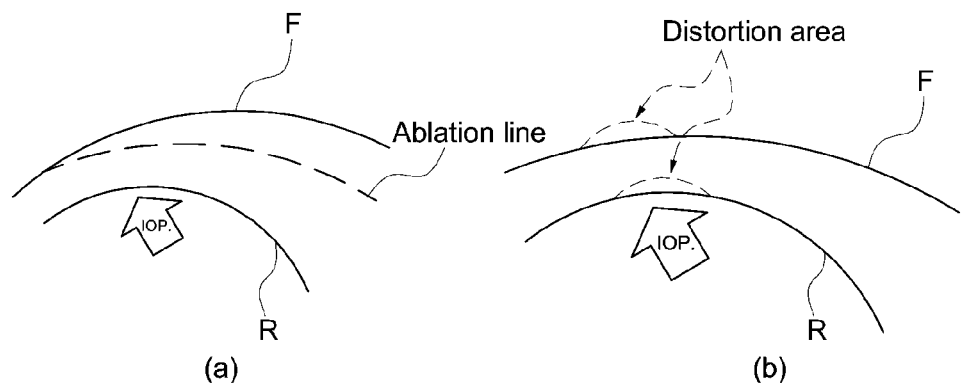
FIG. 3 is a sectional view showing an asymmetric cornea before myopic correction in a region where corneal ablation is performed, and showing a shape of the asymmetric cornea being distorted due to corneal distortion caused by intraocular pressure after the ablation.

As shown in FIG. 3, the asymmetric cornea (corneal distortion) is caused by the intraocular pressure (hereinafter referred to as "IOP") concentrated in a thin peripheral cornea so as to allow the peripheral cornea to protrude from the inside to the outside. This leads to corneal distortion occurring in a partial shape or the entire shape of the cornea.

Figure 4:
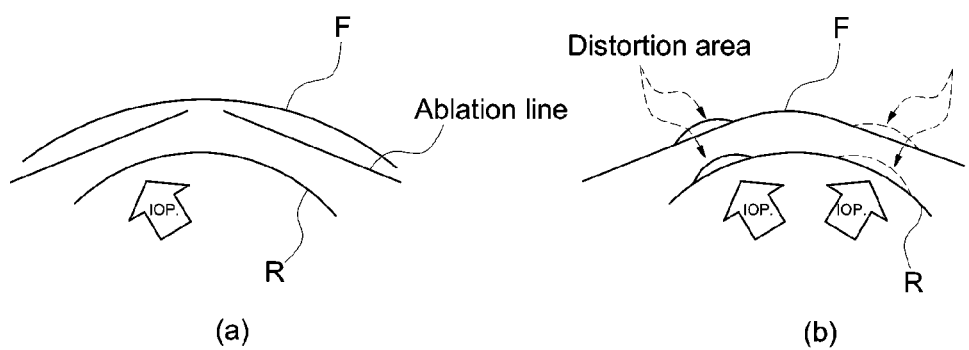
FIG. 4 is a sectional view showing the asymmetric cornea before hyperopic correction in a region where corneal ablation is performed, and showing a shape of the asymmetric cornea being distorted due to corneal distortion caused by intraocular pressure after the ablation.

In detail, FIG. 3 is a sectional view showing an asymmetric cornea before myopic correction in a region where corneal ablation is performed, and showing a shape of the asymmetric cornea being distorted due to corneal distortion caused by intraocular pressure in region that is thinned after the ablation according to the conventional method. FIG. 4 is a sectional view showing the asymmetric cornea before hyperopic correction in a region where corneal ablation is performed, and showing a shape of the asymmetric cornea being distorted due to corneal distortion caused by intraocular pressure in a region that is thinned after the ablation according to the conventional method.

The distorted region of the cornea allows the progress of light converged on a retina from a fixation point to deviate from a visual axis so that the focus is dispersed, thereby generating visual discomfort such that an object is seen as distorted or blurred.

The degree of visual discomfort due to the defective shape of the cornea is easily determined through a case in which there is corneal astigmatism. Astigmatism measured in an elliptic axial-symmetric cornea is a type of defective shape when compared to a spherical point-symmetric cornea. The astigmatism of 1.5 diopter (spherical equivalent=0.75 diopter) is considered to have visual discomfort, and in this case, the ratio of corneal shape defect is within 2% of the average curvature of 43 D (i.e., 0.75 D/43 D≈0.01744). Therefore, it means that, even if the shape of the cornea is distorted only by 2%, it is necessary for the defective shape to be corrected for vision improvement.

If the cornea is cut in order to correct the curvature error only by the conventional method without making the cornea as the symmetric cornea by correcting the defective shape of the asymmetric cornea through correcting the thickness deviation in view of point symmetry, as shown in FIGS. 3 and 4, the intraocular pressure is concentrated in the mid-peripheral or peripheral part of the cornea, which is thin after the cutting, while generating shape distortion. At this time, the light passing through the distorted part of the cornea deviates from the visual axis, and the focus is dispersed, so that a glare symptom such as coma aberration and a phenomenon such as image distortion are incurred, thereby deteriorating visual acuity.

Therefore, the present invention prevents the shape distortion of the cornea by eliminating the concentration of the intraocular pressure according to the thickness deviation in the mid-peripheral or peripheral part of the cornea, which is different from the conventional corneal ablation method in which only the curvature error is improved when corneal ablation is performed for correcting the asymmetric cornea. In addition, an equipment and a method for creating a corneal ablation plan and performing ablation on the cornea with a laser are proposed, in which the shape of the cornea is corrected so as to be symmetric and have the posterior corneal cone located only at the central portion of the cornea by concentrating the intraocular pressure only in the central portion of the cornea, so that the side effect of visual acuity being deteriorated again due to postoperative shape distortion can be prevented.

In addition, the method of improving visual defects due to the above-described shape distortion included in the asymmetric cornea is executed together with the existing curvature error correction method. In addition, I propose a method of increasing the range of surgery application and of vision improvement more than the conventional method, by eliminating the curvature error while removing the glare symptom such as the coma aberration and the phenomenon such as image distortion.

Figure 5:
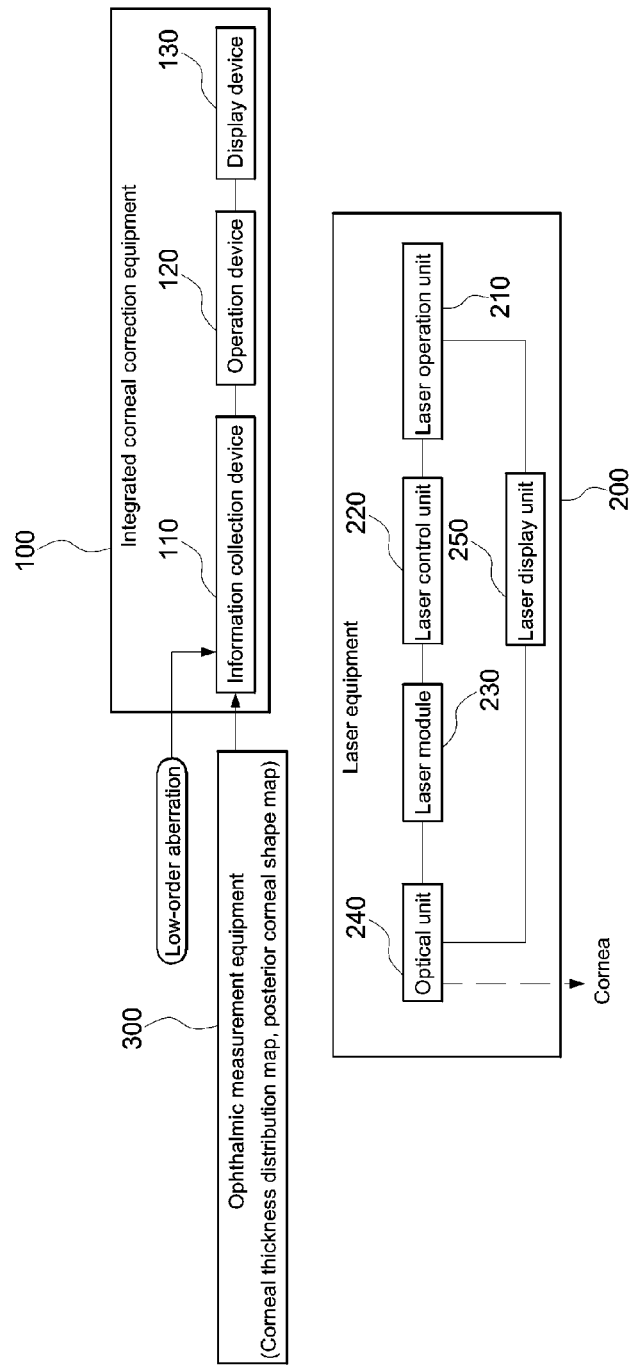
FIG. 5 is a block diagram showing a corneal ablation system for integrally correcting defective shape and curvature error according to the first embodiment of the present invention.

FIG. 5 is a block diagram showing a corneal ablation system according to the first embodiment of the present invention, in which integrated correction equipment used for integrally correcting defective shape and curvature error is installed on the outside in collaboration with the laser equipment.

Figure 6:
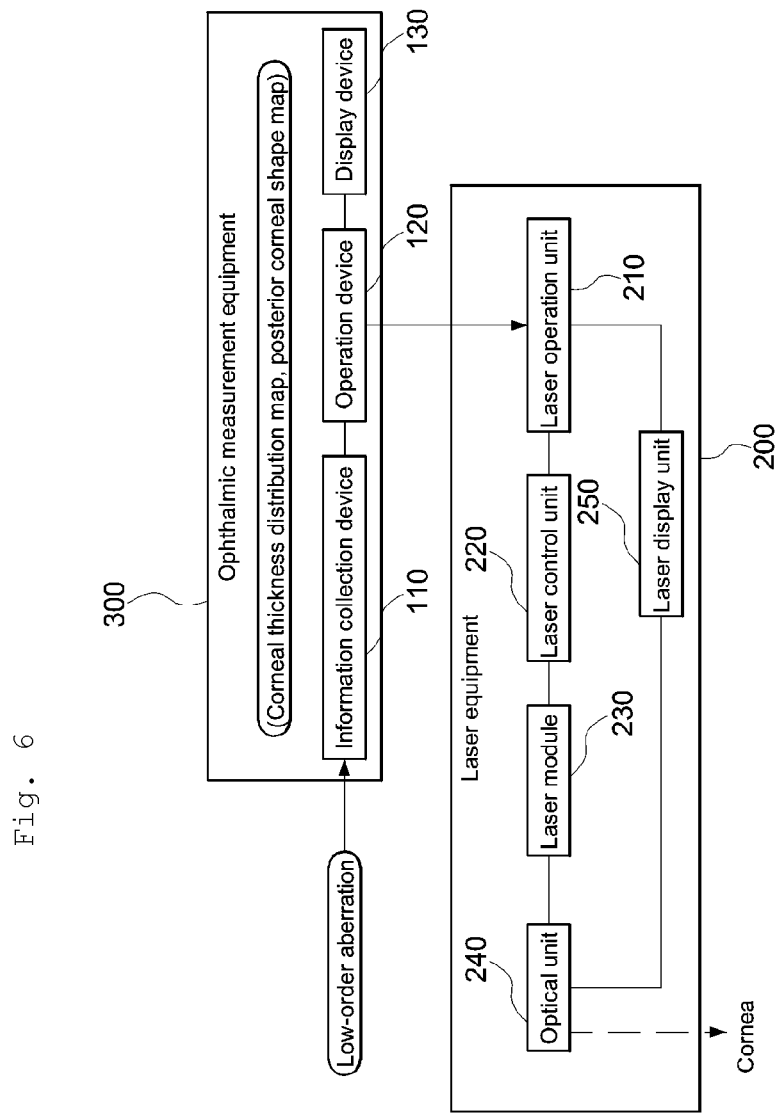
FIG. 6 is a block diagram showing that the integrated corneal correction equipment according to the second embodiment of the present invention is installed in an ophthalmic measurement equipment.
Figure 7:
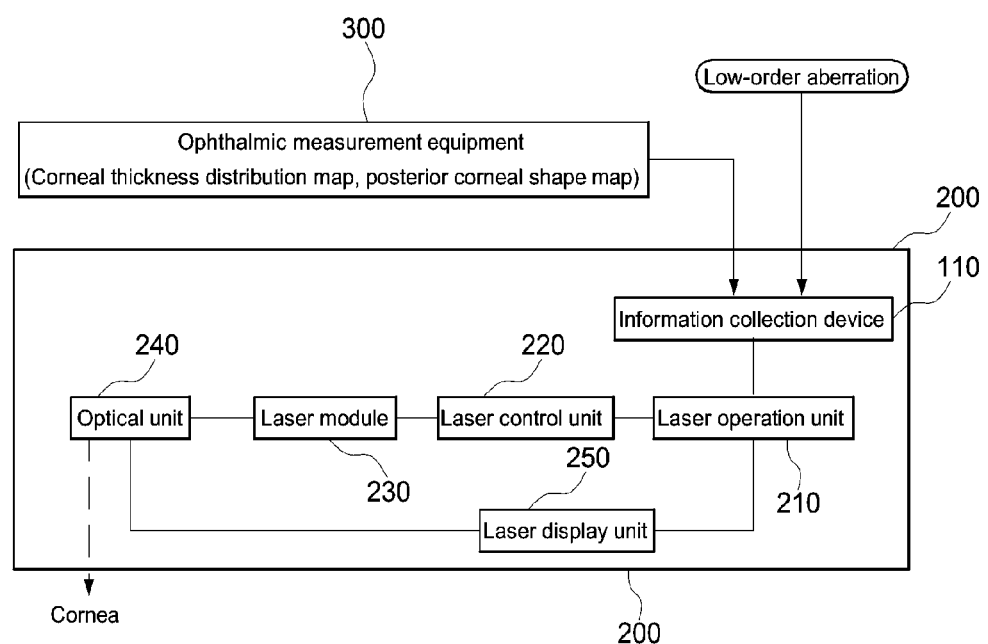
FIG. 7 is a block diagram showing a case of performing integrated corneal correction in laser equipment according to the third embodiment of the present invention.

In addition, FIG. 6 is a block diagram showing that integrated corneal correction equipment according to the second embodiment of the present invention is installed in an ophthalmic measurement equipment and transferred to the laser. FIG. 7 is a block diagram showing a case of performing integrated corneal correction in laser equipment according to the third embodiment of the present invention.

In order to correct the defective shape of the asymmetric cornea and to achieve integrated correction of the low-order aberration, the intraocular pressure has to be concentrated at the central portion of the posterior cornea. In other words, the defective shape of the cornea has to be corrected and the focal distance has to be adjusted, such that the focal direction of the light converged on the retina from the fixation point matches the visual axis, by making the cornea in a symmetric corneal shape that has the posterior corneal cone located at the central portion of the cornea, and also removing the low-order aberration.

Hereinafter, on the idea of the present invention, the equipment for creating a corneal ablation plan and cutting the cornea with the laser will be described in detail, in which the corneal ablation plan is created by applying a method of collecting data required to create an integrated correction plan for the defective shape and the curvature error of the asymmetric cornea and determining the degree of the defective shape of the asymmetric cornea, a partial corneal ablation form used for cutting the peripheral part of the cornea for correcting the defective shape, a partial corneal ablation method for correcting the defective shape, a method of achieving defective shape correction with a symmetric cornea that has the posterior corneal cone located at the central portion of the cornea without fluctuation in the average curvature by offsetting myopic curvature generated when the partial corneal ablation is performed, such that a myopic correction spherical aberration is calculated and the central portion of the cornea is cut, so as to concentrate the intraocular pressure in the cut central portion of the cornea, and an integrated corneal ablation method which interlocks the defective shape correction and the low-order aberration (curvature error) correction so as to achieve both the defective shape correction and the curvature error correction.

First, referring to FIG. 5, integrated corneal correction equipment 100 is independently interposed between an existing ophthalmic measurement equipment 300 and laser equipment 200 according to the first embodiment of the present invention. In this case, the integrated corneal correction equipment 100 of the present embodiment can use the ophthalmic measurement equipment 300 and the laser equipment 200 used in an ophthalmic hospital as they are, so that a highly effective vision correction method of the present invention can be achieved by additionally installing the integrated corneal correction equipment 100.

The integrated corneal correction equipment 100 obtains operation information for controlling an operation of the laser equipment 200 by using low-order aberration information together with corneal thickness distribution map information and posterior corneal shape map information obtained by the ophthalmic measurement equipment 300.

The integrated corneal correction equipment 100 includes: information collection device 110 for collecting corneal shape information on a corneal thickness distribution map and a posterior corneal shape map from the existing ophthalmic measurement equipment 300, and the low-order aberration information of the cornea; and an operation device 120 for creating an integrated corneal ablation plan by using the information collected by the information collection device 110.

In addition, the integrated corneal correction equipment 100 may further include a display device 130 for displaying to a user with the information collected by the information collection device 110, or information on the integrated corneal ablation plan created by the operation device 120 and real-time shape changes according to corneal ablation execution.

In detail, the information collection device 110 constituting the integrated corneal correction equipment 100 of the present embodiment collects information on the corneal thickness distribution map, the posterior corneal shape map, and the low-order aberration.

The operation device 120 creates the partial corneal ablation plan to reduce the thickness deviation of the cornea based on the collected the posterior corneal shape map and corneal thickness distribution map. In addition, the operation device 120 calculates the same amount of spherical aberration so as to create a myopic correction corneal ablation plan to relieve a value of myopic curvature fluctuation generated during partial ablation of the cornea. Further, the operation device 120 creates the integrated corneal ablation plan by calculating an interlocking low-order aberration that can be combined with the partial corneal ablation plan by summing up the calculated spherical aberration with the low-order aberration, and combining the partial corneal ablation for shape correction with corneal ablation for correcting the interlocking low-order aberration. In addition, the associated simulation map is completed.

The display device 130 displays the integrated corneal ablation plan and the associated simulation map transmitted from the operation device 120 to allow a surgeon to examine whether an ablation pattern is correct before shooting the laser by comparing the integrated corneal ablation plan and the associated simulation map with the posterior shape map or thickness distribution map of the cornea before the ablation.

Meanwhile, the laser equipment 200 includes: a laser operation unit 210 for receiving the integrated corneal ablation plan from the operation device 120 of the integrated corneal correction equipment 100 to perform an operation for the corneal ablation; a laser control unit 220 for controlling a laser module 230 by using laser control information calculated by the laser operation unit 210; the laser module 230 of which an operation is controlled according to the laser control unit 220, for generating a laser; and an optical unit 240 for changing optical characteristics or providing an optical path so as to irradiate the cornea with the laser.

In addition, the laser equipment 200 may further include a laser display unit 250 for allowing a user to confirm information on the laser irradiated by the optical unit 240, a process that the laser operation unit 210 performs an operation for cutting the cornea by using the integrated corneal ablation plan and the result of the process.

The laser display unit 250 displays the corneal ablation plan, a corneal ablation execution scene, and the changes of the simulation map through a monitor.

Hereinafter, a process and a method for creating the integrated corneal ablation plan by the integrated corneal correction equipment 100 according to the present embodiment will be described in detail.

First, in order for the integrated corneal correction equipment 100 to create the integrated correction plan for the defective shape and the curvature error of the asymmetric cornea, information on the posterior corneal shape map, the corneal thickness distribution map and the low-order aberration (including the spherical aberration and astigmatism) is required.

However, astigmatism can be classified as astigmatism due to a defective corneal shape and as astigmatism due to curvature error. In the case of astigmatism due to the defective corneal shape, astigmatism is caused by the thickness deviation in two parts, which are symmetric parts about an astigmatic axis. In the case of astigmatism due to curvature error, astigmatism occurs despite the absence of thickness deviation in the two parts that are symmetric about the astigmatic axis.

In other words, the information required to analyze the defective corneal shape is information on the posterior corneal shape map and the corneal thickness distribution map, and information on astigmatism incurred due to the defective corneal shape.

In addition, the information required for correcting the curvature error is information on astigmatism incurred by the spherical aberration and the curvature error among the low-order aberrations.

Among this information, the posterior corneal shape map is used for determining whether the cornea is an asymmetric cornea with visual axis deviation, and which direction the thickness deviation of the cornea should be reduced, by detecting an eccentric position of the posterior corneal cone.

The corneal thickness distribution map is used for detecting the thickness deviation of the cornea. If there is astigmatism, firstly, the thickness deviation of two symmetric parts about the astigmatic axis is detected and the astigmatism due to the defective shape is corrected by relieving the corneal thickness deviation. Next, partial corneal ablation shape, size, and amount in the periphery part of the cornea are determined so as to relieve the thickness deviation in view of the point symmetry.

In addition, in order to reduce the thickness deviation, the myopic curvature value generated when partially cutting the peripheral cornea is calculated using the same spherical aberration, and the curvature fluctuation is offset through the myopic correction corneal ablation. Through the offset, a corneal ablation plan is created for the corneal shape correction without fluctuation in the average curvature value. If astigmatism is corrected by the partial corneal ablation, the average curvature value of the cornea is deducted as much as the corrected value. Thereafter, when the cornea is cut by interlocking the correction of the low-order aberration for removing the curvature error, an astigmatic value corrected by the partial corneal ablation is reduced and reflected.

Meanwhile, astigmatism due to the spherical aberration and the curvature error among the collected low-order aberrations can be relieved by the existing low-order aberration correction method. Thus, the integrated corneal ablation plan where the defective shape and the curvature error are collectively corrected, is completed by combining the corneal ablation plan for the corneal shape correction with the existing corneal ablation plan for the low-order aberration correction.

Next, a method of determining the defective shape and a distortion degree of the asymmetric cornea will be described.

First, it is necessary to determine whether the shape of the cornea is asymmetric, and if the shape of the cornea is asymmetric, it is necessary to make an accurate determination about the distortion region.

In the posterior corneal shape map, the posterior corneal cone represents the protrusion in the posterior cornea due to the concentration of intraocular pressure in a thinner region. The distorted part of the asymmetric cornea can be detected through a shape of the posterior corneal cone which is eccentric in the mid-peripheral part or peripheral part of the posterior cornea.

Figure 15:
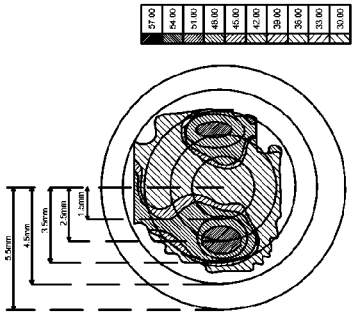

Therefore, the position and shape of the posterior corneal cone can be detected by using the posterior corneal shape map as shown in FIG. 15, in which distortion of the corneal shape and the asymmetric shape are shown. In addition, the degree of distortion can be determined from thickness deviation distribution based on the thickness distribution map.

FIG. 15 is a view showing distortion of the cornea according to a position of a protruding portion of the cornea, that is, the posterior corneal cone, and a method of correcting the distortion.

The above-described partial corneal ablation form for the defective shape correction is the same as the ablation form 2 shown in FIG. 16. In detail, the partial corneal ablation form is the same as a semi (½)-cylinder astigmatic ablation form, which is an existing astigmatism removal scheme using the laser and serving as a part of a cylinder (+) astigmatic ablation form for cutting two portions of the cornea facing each other in view of axial symmetry in a same semi (½)-cylinder shape, or a form where curvature fluctuation based on existing ablation shape and amount is generated in direct proportion. The spherical aberration capable of offsetting the value of the myopic curvature fluctuation generated when the partial corneal ablation is performed at the peripheral part of the cornea is accurately calculated, so that the curvature error is completely removed even when the integrated correction where the partial corneal ablation form is included in the conventional ablation for removing the low-order aberration is performed.

A quarter (¼) cylinder astigmatic ablation form disclosed in the ablation form 3 shown in FIG. 16 is obtained by dividing the semi(½)-cylinder astigmatic ablation form in half (½) again. The quarter (¼) cylinder astigmatic ablation form is used for reducing minute thickness deviation which remains after the thickness deviation is reduced by using the semi-cylinder astigmatic ablation form.

Hereinafter, the partial corneal ablation method for cutting the partial cornea at the peripheral part of the cornea and the central portion of the cornea to correct the defective shape will be described.

The method maximally reduces the thickness deviation of the cornea in view of point symmetry based on the information on the overall corneal thickness distribution map, and relieves the eccentric posterior corneal cone by dispersing the intraocular pressure concentrated in the distorted region. In addition, the method partially cuts the peripheral and central portion of the cornea except for the part where the eccentric posterior corneal cone is present so as to make the cornea into a symmetric cornea, so that the defective shape is corrected into the symmetric cornea that has the posterior corneal cone located at the central portion of the cornea.

Figure 17:
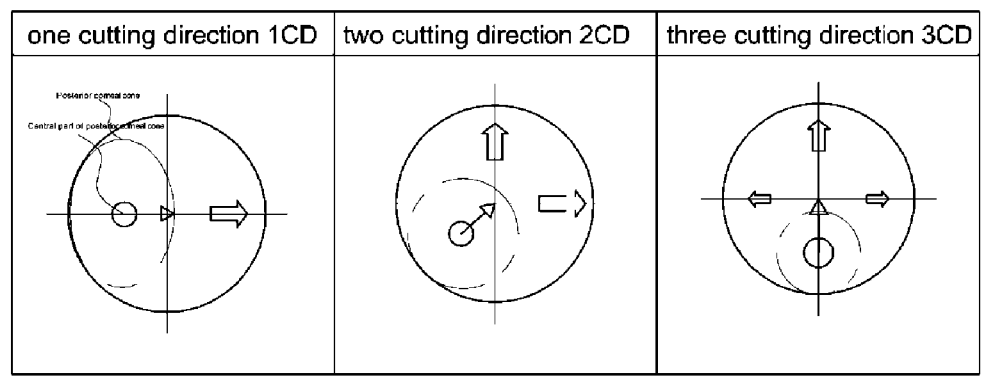

FIG. 17 shows an example of a partial corneal cutting direction for removing the eccentric posterior corneal cone and relocating the posterior corneal cone to the central portion of the cornea.

In order to locate the eccentric posterior corneal cone to the central portion of the cornea, the principle of vector synthesis is applied as shown in FIG. 17. In other words, the partial corneal ablation shape, size, and amount are determined according to the cutting direction in the thick region of the cornea, and the thickness deviation is reduced in view of point symmetry or axial symmetry.

The semi-cylinder astigmatic ablation form can be abbreviated as SA (semi-cylinder ablation), the quarter cylinder astigmatic ablation form can be abbreviated as QA (quarter cylinder ablation), and the cutting direction can be abbreviated as CD (cutting direction). For example, three semi-cylinder astigmatic ablation for cutting in two directions can be represented by 2CD/3SA, and one semi-cylinder astigmatic ablation and one quarter cylinder astigmatic ablation for cutting in one direction can be represented by 1CD/1SA+1QA.

FIG. 18 is a view showing a method of relocating the center of the eccentric posterior corneal cone by using semi (½)-cylinder astigmatic ablation.

FIG. 19 is a view showing an example of partial corneal ablation for preventing corneal protrusion and an example of minute thickness deviation ablation. 3CD/3SA and 4CD/4SA methods are performed for the partial corneal ablation for preventing corneal protrusion in the peripheral part of the cornea, and a 1CD/1QA method is performed for the minute thickness deviation ablation.

Figure 20:
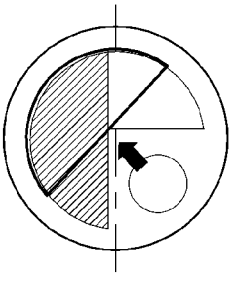

FIG. 20 is a view for explaining a case where overlapping ablation is performed at the central portion of the cornea in order to remove the thickness deviation at the central portion of the cornea during the partial corneal ablation.

The partial corneal ablation for the defective shape correction maximally reduces the thickness deviation in view of point symmetry, basically as shown in the ablation form 2 of FIG. 16, by using the semi (½)-cylinder astigmatic ablation form. In this case, the ablation method is shown in FIG. 18 to FIG. 20.

As shown in FIGS. 18 to 20, in order to suppress the occurrence of astigmatism, the form may be enlarged by basically overlapping the form half by half or may use a method of overlapping and cutting the form at the central portion as a basic principle. The form may be used to entirely or partially overlap ablation regions if necessary.

The partial corneal ablation position may be arbitrarily selected from 1° to 360°, and the thickness deviation is reduced in the semi-cylinder form as described above. Next, in order to minimize the residual thickness deviation, the quarter cylinder form as shown in the ablation form 3 of FIG. 16 is used in the same manner as described above. In addition, since the ablation amount is very small, direct ablation is performed on a region having the residual thickness deviation without worrying about the occurrence of astigmatism.

A method of maximally reducing the thickness deviation of a point-symmetric cornea to eliminate the thickness deviation will be described in detail. It is to remove the eccentric posterior corneal cone of the asymmetric cornea and form the posterior corneal cone at the central portion of the cornea as shown in FIGS. 18 to 20, by using the partial corneal ablation form shown in FIG. 17 described above.

One-Direction Ablation (1CD)

In one-direction ablation, as shown in FIG. 21, when one of two portions of the peripheral cornea to be cut axial-symmetrically for astigmatism correction is thick and has a thickness deviation, only the thick portion of the cornea is subjected to one semi-cylinder astigmatic ablation (1SA) form to reduce the thickness deviation. The one-direction ablation is mainly used for correcting astigmatism due to the defective corneal shape.

Two-Direction Ablation (2CD)

Two-direction ablation can be performed when the thick portion of the cornea is formed in an "L" shape. Directions of the two semi-cylinder astigmatic ablation (2SA) are overlapped and connected with each other at an angle of 90° to prevent astigmatism from occurring.

Three-Direction Ablation (3CD)

Three-direction ablation can be performed when the thick portion of the cornea is formed in a "U" shape. Three semi-cylinder astigmatic ablation forms are connected to each other while overlapping at an angle of 90°, and an ablation ratio of the central portion and overlapped left and right sides of semi-cylinder astigmatisms is set as 2:1:1 to prevent astigmatism.

In particular, when the corneal protrusion progresses, the thickness deviation at the remaining portion except for a protruding portion is removed by using the three-direction ablation (3CD) or a four-direction ablation (4CD) in order to prevent the concentration of the intraocular pressure at the protruding portion. By removing the thickness deviation, the intraocular pressure can be dispersed. The ablation amount of each portion is different from each other, and even if curvature fluctuation and astigmatism occur, ablation is not performed on the central portion of the cornea.

Center Overlapping Ablation

In the center overlapping ablation, one semi-cylinder astigmatic ablation (1SA) is performed to reduce the thickness at an internal angle (45°) region, which is a central portion of two semi-cylinder astigmatisms adjacent to each other in the perpendicular direction after performing the two, three, and four-direction ablation (2CD, 3CD, and 4CD). Further, if necessary, one quarter cylinder astigmatic ablation (1QA) can be additionally performed.

In order to remove the remaining deviations after thickness deviation ablation is performed through a semi-cylinder, the center overlapping ablation is performed after minute thickness deviation ablation and the one-direction corneal ablation (1CD). In this case, one quarter cylinder astigmatic ablation (1QA) is performed.

Hereinafter, the process of creating the partial corneal ablation plan as described above will be described.

First, the thickness deviation in the peripheral part of the cornea is maximally reduced in view of point symmetry, so as to make the cornea have a point-symmetric shape where the posterior corneal cone is located at the central portion of the cornea.

Second, when the thickness deviation is symmetric about a cylinder (+) astigmatic axis, the thickness deviation is removed through a one-direction corneal ablation plan, and the astigmatism caused by the defective shape is relieved.

Third, the thick part located on the opposite side in view of point symmetry except for the position of the eccentric posterior corneal cone is cut to minimize the thickness deviation, and the ablation amounts at both symmetric portions about a vertical center axis of a region, which is pre-cut to prevent astigmatism from occurring, are identical to or different from each other so as to minimize the thickness deviation.

Fourth, by using the first and second methods, the thickness deviation is reduced in view of point symmetry, in which the reduction starts from a portion having large thickness deviation and gradually moves to a portion having small thickness deviation.

Fifth, when it is difficult to uniformly reduce the thickness deviation in view of point symmetry by using the method as described above while locating the posterior corneal cone at the central portion of the cornea, the thickness in upper and inner (nasal) portions of the cornea is cut to be thinner than the thickness of lower and outer (temporal) portions of the cornea. The cutting makes the curvature deviation of the cornea correspond to a convergence angle of both eyes and patterns of the reading direction, thereby providing convenient life vision.

Hereinafter, a method of correcting the defective shape will be described.

In the case of partial corneal ablation, the method of correcting the defective shape without fluctuation in the corneal curvature by offsetting the generated myopic curvature calculates the same amount of spherical aberration that may relieve the value of the myopic curvature fluctuation generated when the partial corneal ablation is performed. Then, the spherical aberration calculated by using a conventional myopic correction ablation method is applied to cut the central portion of the cornea by the myopic correction corneal ablation, thereby preventing curvature fluctuation. At this time, in order to calculate the spherical aberration that is equal to the magnitude of the curvature fluctuation generated when the partial corneal ablation as described above is performed, a curvature fluctuation offset formula of the present invention is used in the method shown in FIGS. 8 to 11.

FIGS. 8 to 11 are views showing an example of calculating a spherical aberration for offsetting curvature fluctuation due to partial corneal ablation according to the present invention.

Figure 8:
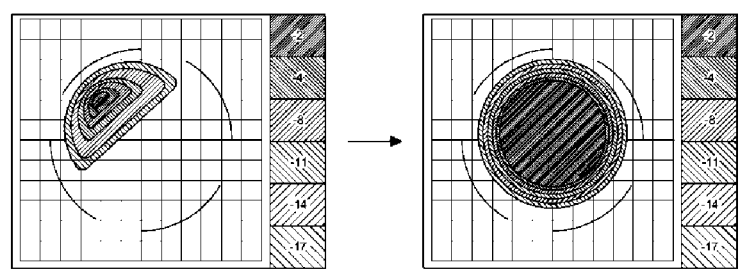
FIGS. 8 to 11 are views showing examples of calculating spherical aberration for offsetting curvature fluctuation due to partial corneal ablation according to the present invention.

In the case of FIG. 8, the ablation at the central portion of the cornea is offset with the curvature fluctuation value Sph.=−0.25 D when cutting the cornea with one semi-cylinder astigmatism (1SA) in 1 D. In addition, the curvature fluctuation value is 1×0.25=0.25 Sph. D.

Figure 9:
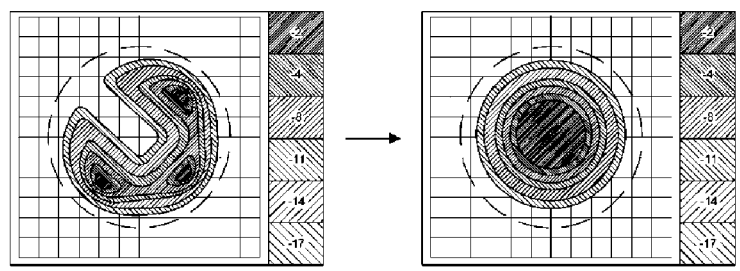

In the case of FIG. 9, the ablation at the central portion of the cornea is offset with the curvature fluctuation value Sph.=−0.75 D, in which three semi-cylinder astigmatisms (3SA) are used. In addition, the curvature fluctuation value is 3×0.25=0.75 Sph. D.

Figure 10:
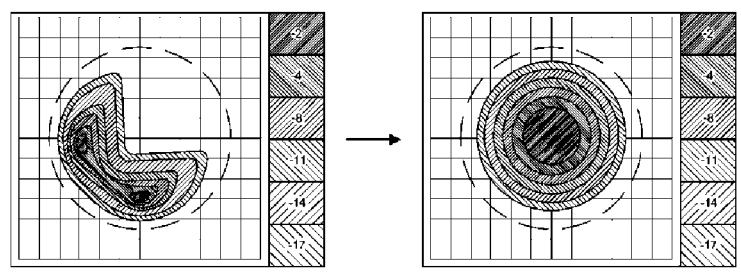

In the case of FIG. 10, the ablation at the central portion of the cornea is offset with the curvature fluctuation value Sph.=−0.5 Diopter when cutting the cornea with two semi-cylinder astigmatisms (2SA) in 1 D. In addition, the curvature fluctuation value is 2×0.25=0.5 Sph. D.

Figure 11:
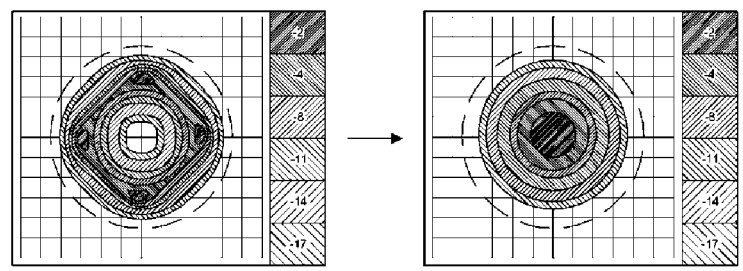

In the case of FIG. 11, the ablation at the central portion of the cornea is offset with the curvature fluctuation value Sph.=−1.0 D when cutting the cornea with four semi-cylinder astigmatisms (4SA) in +1 D. In addition, the curvature fluctuation value is 4×0.25=1 Sph. D.

Figure 12:
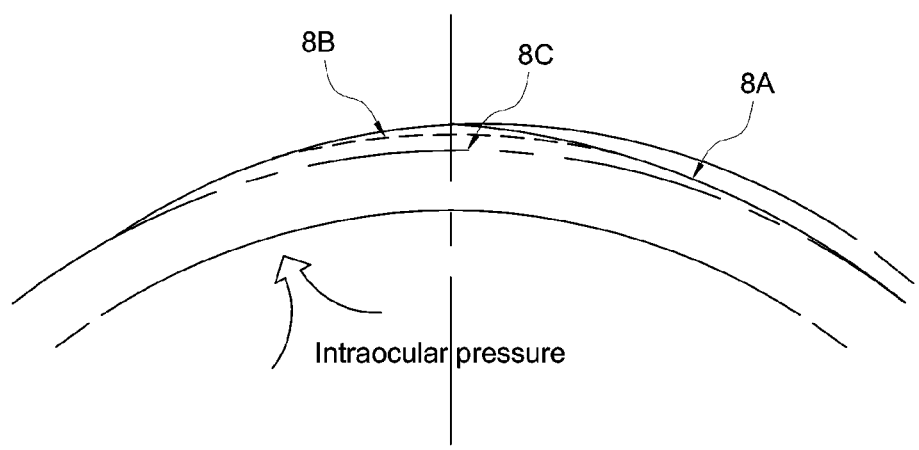
FIG. 12 is a view for explaining an integrated corneal ablation method according to the present invention.

FIG. 12 is a view for explaining an integrated corneal ablation method according to the present invention.

The cornea is shown in which the intraocular pressure is concentrated on a thinner cornea region on the left side. In the corneal ablation for the integrated correction of the asymmetric cornea that has the posterior cornea protruding toward the front, ablation on the partial cornea at the peripheral part is firstly performed (8A).

Next, the spherical aberration for offsetting the curvature fluctuation due to the partial corneal ablation is calculated, and then the central portion of the cornea is cut (8B). Then, the cornea is cut for correcting the existing curvature error (8C). In this process, the spherical aberration for offsetting the curvature fluctuation and the collected low-order aberration that is inherently present in the cornea are summed up in the calculation process to calculate the interlocking low-order aberration to be combined with the partial corneal ablation plan. In addition, in the ablation process using the laser, the partial corneal ablation for shape correction and the corneal ablation for correcting the calculated interlocking low-order aberration are combined and executed in one session.

As illustrated in FIG. 12, the curvature value generated during the one semi-cylinder astigmatic ablation can be easily calculated, in which the curvature value is 0.5 times the conventional astigmatic correction value, and 0.25 times the spherical aberration correction value. Therefore, the spherical aberration for myopic correction, which can prevent the curvature fluctuation due to the partial corneal ablation, can be calculated by the following curvature fluctuation offset formula.

Curvature Fluctuation Offset Formula

Spherical aberration for myopic correction required for offsetting curvature fluctuation=−0.25 [total of semi(½)-cylinder astigmatic ablation amounts (Diopter)]=−0.125 [total of quarter cylinder astigmatisms (Diopter)]

If the symmetric cornea having no curvature fluctuation for shape correction is combined with corneal ablation for low-order aberration correction, by the method described above, integrated vision correction where the defective shape and the curvature error of the asymmetric cornea are integrally corrected can be achieved.

Therefore, integrated vision correction method reduces the thickness deviation of the cornea by cutting the thick portion of the peripheral part of the cornea in view of point symmetry to remove the eccentric posterior corneal cone. In addition, corneal distortion is relieved through the reduction of the thickness deviation. The same amount of spherical aberration capable of offsetting the myopic curvature caused by the partial corneal ablation is calculated.

In addition, the interlocking low-order aberration is calculated by summing up the spherical aberration with the conventional low-order aberration, and the partial corneal ablation for correcting the defective shape is interlocked and executed with the conventional curvature correction method for removing the interlocking low-order aberration. In this case, the curvature error is removed, the thickness deviation at the peripheral part of the cornea is maximally reduced, and the shape of the cornea is corrected into the symmetric cornea that has the posterior corneal cone generated at the central portion of the cornea due to the concentration of the intraocular pressure, thereby achieving the integrated vision correction.

Once the integrated corneal correction plan is created by the method as described above, the information is transmitted to the laser equipment 200. In addition, the laser control unit 220 of the laser equipment 200 controls the laser according to the cornea ablation plan transmitted through the laser operation unit 210 so as to execute the corneal ablation.

In addition, the laser display unit 250 displays a simulation according to the corneal ablation plan, an ablation scene when executing the corneal ablation, and change of the simulation map in real time.

Further, the laser is irradiated onto the cornea to perform corneal ablation based on the integrated corneal ablation plan transmitted from the laser control unit 220. At this time, the thickness deviation is reduced in view of point symmetry to generate the eccentric posterior corneal cone at the central portion of the cornea, while eliminating the curvature error, so that the defective shape and the curvature error are corrected together.

In addition, all of the ablation processes can be confirmed in real time through the laser display unit 250, in which the graphical change of the simulation and the actual scene can be confirmed.

In the corneal ablation method using the laser, which performs the integrated corneal ablation according to the integrated corneal ablation plan, only the corneal ablation for correcting the defective shape without the curvature fluctuation is performed in the case of the asymmetric cornea with no low-order aberration. The corneal ablation for integrated correction is performed, and corneal ablation for correcting the low-order aberration is performed in the case of the symmetric cornea.

Figure 13:
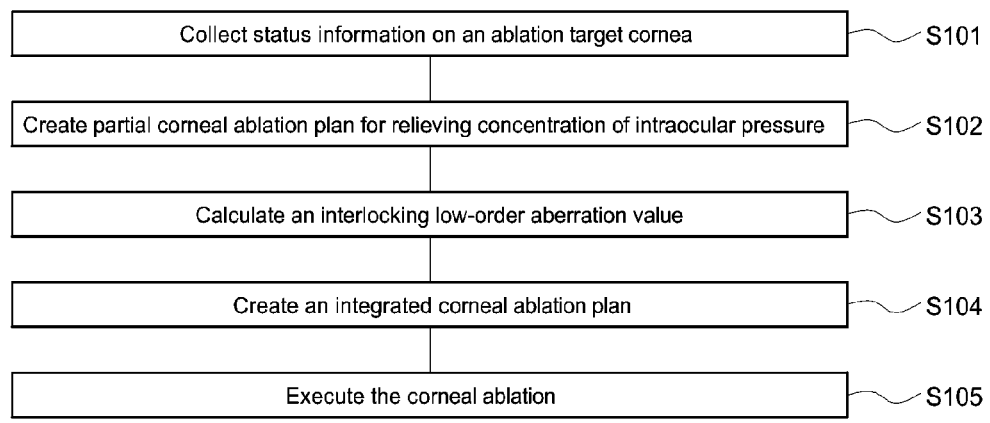
FIG. 13 is a flowchart showing the process of cutting the cornea according to an integrated corneal ablation plan according to the present invention.

FIG. 13 shows a flow in which the integrated corneal ablation plan is created by the integrated corneal correction equipment 100 according to the present invention, and the cornea is cut according to the integrated corneal ablation plan.

FIG. 13 is a flowchart showing a process of cutting the cornea according to an integrated corneal ablation plan according to the present invention.

First, integrated corneal correction equipment for the integrated corneal correction is provided, and corneal status information of the ablation subject is collected (S101).

In addition, the operation device 120 of the integrated corneal correction equipment 100 constituting the integrated corneal ablation system creates a partial corneal ablation plan in which the thickness deviation is maximally reduced in view of point symmetry with respect to peripheral portions excluding the posterior corneal cone to relieve the concentration of intraocular pressure which is eccentric in the peripheral part of the cornea, based on the collected corneal status information (S102).

Next, the same amount of spherical aberration value is summed up with the collected low-order aberration in order to offset the myopic curvature fluctuation value generated when performing the partial corneal ablation plan. In addition, the interlocking low-order aberration value for interlocking the defective shape correction achieved through the partial corneal ablation with the curvature error correction is calculated (S103).

Thereafter, the integrated corneal ablation plan is created by combining the partial corneal ablation plan with the corneal ablation plan for removing the calculated interlocking low-order aberration (S104). In addition, the laser control unit 220 controls the laser module 230 based on the integrated corneal ablation plan created by the operation device 120 to irradiate the cornea with the laser to cut the cornea, so that the curvature and the shape can be simultaneously corrected (S105).

As shown in FIG. 5, the above embodiments are based on the configuration that the integrated corneal correction equipment 100 is interposed between the ophthalmic measurement equipment 300 and the laser equipment 200 to create the integrated corneal ablation plan and transmit the integrated corneal ablation plan to the laser equipment 200.

However, as shown in FIG. 6, it is also possible that the information collection device 110, the operation device 120, and the display device 130 constituting the integrated corneal correction equipment are installed in the ophthalmic measurement equipment 300.

In addition, as shown in FIG. 7, the information collection device 110 constituting the integrated corneal correction equipment of the present invention is installed in the laser equipment 200. It is also possible that the laser operation unit 210 of the laser equipment 200 serves as the operation device 120 and the laser display unit 250 of the laser equipment 200 serves as the display device 130.

However, for convenience of explanation, as shown in FIG. 5, it will be described mainly about the case where the integrated corneal correction equipment 100 is interposed between the ophthalmic measurement equipment 300 and the laser equipment 200.

Figure 14:
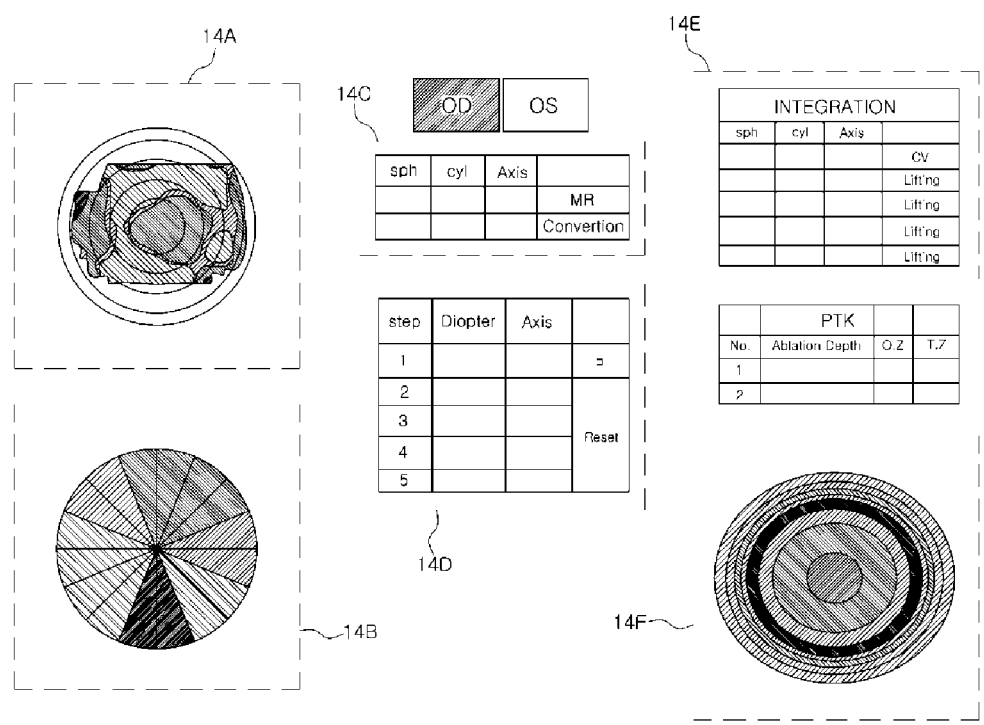
FIG. 14 is a view showing one example of a program in which an integrated corneal correction plan is created according to the present embodiment.

FIG. 14 is a view showing one example of a program in which an integrated corneal correction plan is created according to the present embodiment.

14A is an example of the posterior corneal shape map, which is used to check indications and determine the direction of creating a surgical plan, and 14B is a corneal thickness distribution map showing the thickness deviation expressed in colors (shown as hatching) together with numerical values.

14C is a procedure that allows to easily confirm the thickness deviation based on the astigmatic symmetry axis by converting the low-order aberration in the existing corneal ablation method using the laser, and reflecting the converted low-order aberration in the simulation.

14D is an interface for creating the partial corneal ablation plan to reduce the thickness deviation, and the ablation shape and size are indicated in the simulation map 14F. In addition, the thickness of the central portion of the cornea, which will be reduced by the partial corneal ablation plan and the myopia correction corneal ablation for offsetting the curvature fluctuation, is automatically displayed through the corneal thickness distribution map 14B as soon as the plan is created.

When the partial corneal ablation plan is created in 14D, the interlocking low-order aberration is automatically calculated and inputted to the interlocking low-order aberration interface 14E, and the created partial corneal plan is also immediately entered into an item LIFTING of the interlocking low-order aberration interface 14E.

The simulation map 14F is displayed according to the integrated corneal ablation plan created through the interlocking low-order aberration interface 14E.

The display device 130 of the integrated corneal correction equipment of the embodiment uses a computer program that provides the interface shown in FIG. 14. By using the computer program, the integrated corneal ablation plan and the associated simulation map can be completed and displayed on a computer monitor.

The information collection device 110 collects information that includes the corneal thickness distribution map, the posterior corneal shape map, and the low-order aberration, which are required for creating the integrated corneal ablation plan, and transmits the collected information to the operation device 120.

In addition, as shown in FIG. 14, the operation device 120 creates the partial corneal ablation plan to cut the peripheral portion of the cornea except for the eccentric posterior corneal cone in a point-symmetric shape so as to maximally reduce the thickness deviation. Through the cutting, the eccentric posterior corneal cone may be relieved and the cornea may have a symmetric shape.

Thereafter, the curvature fluctuation to be generated when the created partial corneal ablation plan is executed is predicted, so as to calculate the myopic spherical aberration that may be offset through the ablation at the central portion of the cornea. In addition, the interlocking low-order aberration for interlocking with the partial corneal ablation plan is calculated by summing up the myopic spherical aberration with the collected inherent low-order aberration. Through this calculation, the posterior corneal cone is promoted to occur in the central portion of the cornea, because the central portion of the cornea is cut more and the concentration of intraocular pressure grows more than the conventional case of removing the low-order aberration.

The integrated corneal ablation plan and the associated simulation map are completed by combining the created partial corneal ablation plan with the interlocking low-order aberration. The created integrated corneal ablation plan is transmitted to the laser control unit 220, and the simulation map is transmitted to the laser display unit 250.

The laser control unit 220 controls an output of a beam and an operation of a mirror through the laser module corresponding to the integrated corneal ablation plan transmitted from the laser operation unit 210, so that the cornea ablation is performed according to the plan.

The laser display unit 250 provides the ablation process in the graphical change of the integrated corneal ablation simulation according to the corneal ablation and an actual image through the monitor in real time.

Hereinafter, the steps of creating the integrated corneal ablation plan and executing the corneal ablation of the integrated corneal ablation system will be described in detail.

First, an integrated corneal ablation system including an operation device 120 for creating an integrated corneal ablation plan and laser equipment 200 is prepared.

Figure 22:
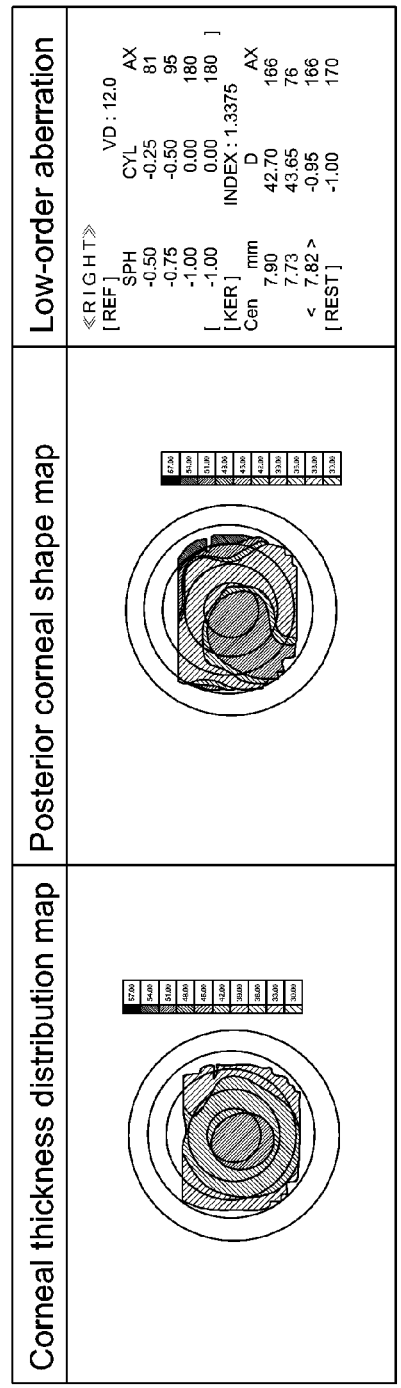

Second, the information collection device 110 collects data including a corneal thickness distribution map, a posterior corneal shape map, and a low-order aberration, as shown in FIG. 22.

Third, the operation device 120 calculates the partial corneal ablation plan and the interlocking low-order aberration based on the data collected by the information collection device 110, and uses the partial corneal ablation plan and the interlocking low-order aberration to create the integrated corneal ablation plan.

The partial corneal ablation plan, which can relieve the eccentric posterior corneal cone by maximally reducing the thickness deviation in view of point symmetry, is created through the operation device 120. Next, when the cornea is cut according to the created partial corneal ablation plan, the myopic curvature fluctuation may occur, so the same amount of spherical aberration is calculated to offset the myopic curvature fluctuation, and the corneal ablation for myopic correction is performed.

Therefore, the operation device 120 calculates in advance the magnitude of the myopic curvature to be generated due to the partial corneal ablation, and the myopic curvature is summed up with the low-order aberration collected by the information collection device 110. In addition, the interlocking low-order aberration for correcting the curvature error together with shape correction that has no fluctuation in the average curvature value is calculated. Thus, the calculated interlocking low-order aberration is combined with partial corneal ablation plan so as to complete the integrated corneal ablation plan. In addition, the integrated corneal ablation simulation map is completed and prepared to be transmitted to the laser control unit 220 and the laser display unit 250.

Fourth, the laser control unit 220 controls the laser module 230 based on the integrated corneal ablation plan created by the operation device 120. Corneal ablation is performed by irradiating with the laser through an optical transmission device. The laser display unit 250 may provide the corneal ablation process together with the shape change of the integrated corneal ablation simulation through a monitor in real-time image.

For the understanding of the present invention, the present invention will be described with reference to some examples and comparative examples.

COMPARATIVE EXAMPLE 1

For the curvature correction, the difference between the two conventional corneal ablation methods and the corneal ablation method for correcting the shape according to the present invention can be seen clearly through comparison.

EXAMPLE 1

A clinical test of performing three semi-cylinder astigmatic ablations (3CD/3SA) in three directions to combine the shape correction with the curvature correction.

Figure 24:
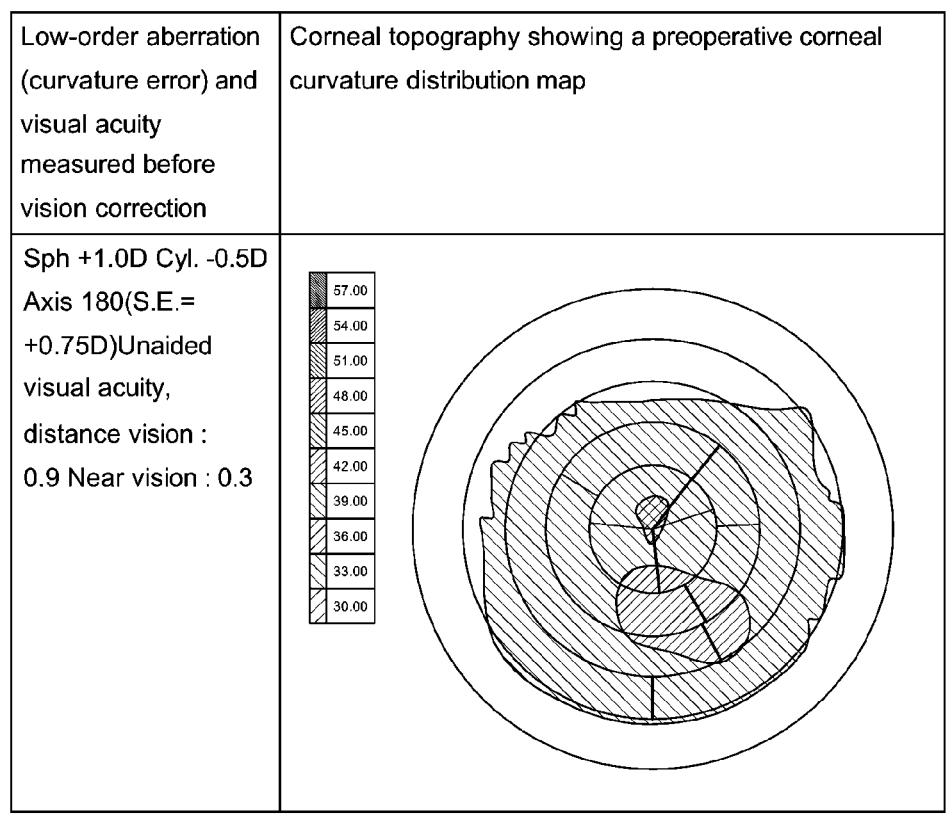

FIG. 24 shows preoperative low-order aberration and vision of the eye to be corrected.

Figure 25:
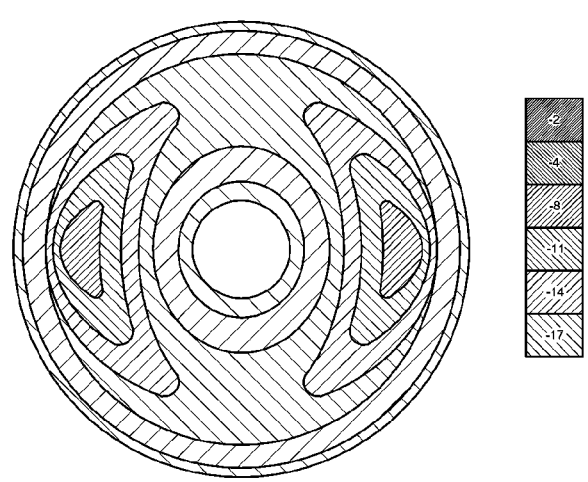

FIG. 25 shows a corneal curvature correction plan according to the existing laser vision correction technique.

Hereinafter, the corneal shape and the integrated curvature correction method according to the present invention will be described.

Figure 26:
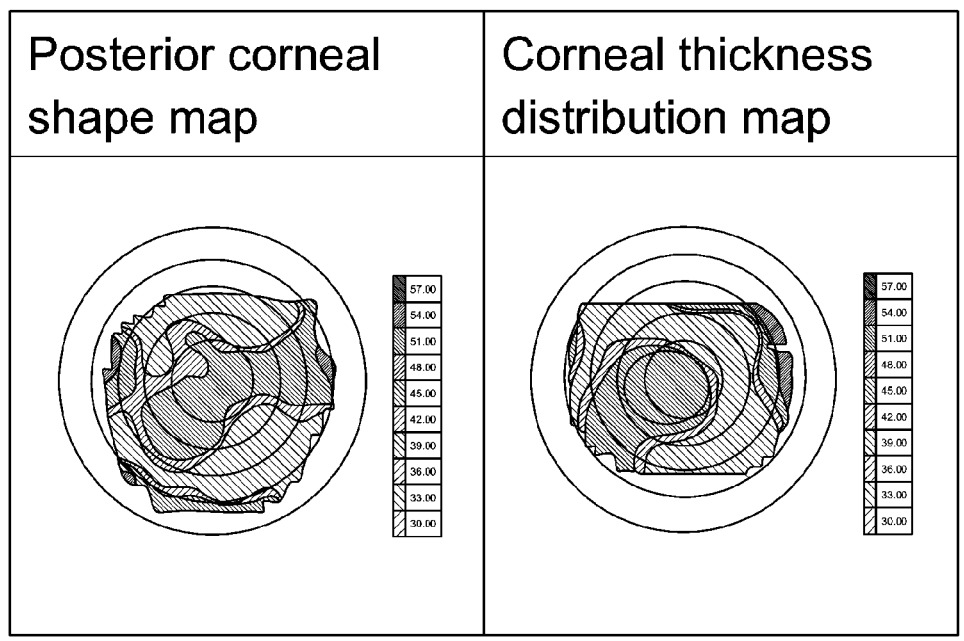

FIG. 26 is a posterior corneal shape map and a corneal thickness distribution map, which are analytical data necessary for shape correction. In addition, the low-order aberration is the same as described above, which is Sph. +1.0 D, Cyl. −0.5 D Axis 180, and the analytical data necessary for the surgical plan where the shape correction and curvature correction are integrated is obtained.

In addition, the ablation plan is created using the integrated corneal ablation program in the following order.

1) The corneal shape is improved by cutting the cornea in three semi-cylinder astigmatic ablation forms by +1.5 D in the three directions including upper, left, and right directions.

2) At this time, since the myopic spherical aberration to be generated is +1.125 D, the spherical aberration to offset the curvature fluctuation is −1.125 D. The calculation formula is 3×1.5 D=4.5 D, and 4.5 D×0.25 D=+1.125 D.

3) When the calculated spherical aberration of −1.125 D is summed up with the pre-measured spherical aberration of the cornea of +1.0 D, the low-order aberration to be corrected is Sph. −0.125 D, Cyl. −0.5 D Axis 180°.

4) In addition, the information thus calculated is inputted to the laser equipment, and the corneal ablation plan is created, in which an approximate value for executing the corneal ablation is Sph. −0.25 D, Cyl. −0.75 D Axis 180°.

5) In order to create the integrated corneal ablation plan, the ablation plan of cutting the cornea in three semi-cylinder astigmatic ablation forms by +1.5 D in the three directions including upper, left, and right directions is integrated with the low-order aberration of Sph. −0.025 D, Cyl. −0.75 D Axis 180° to create the corneal ablation plan. In addition, the corneal ablation simulation is created as shown in FIG. 27.

Figure 27:
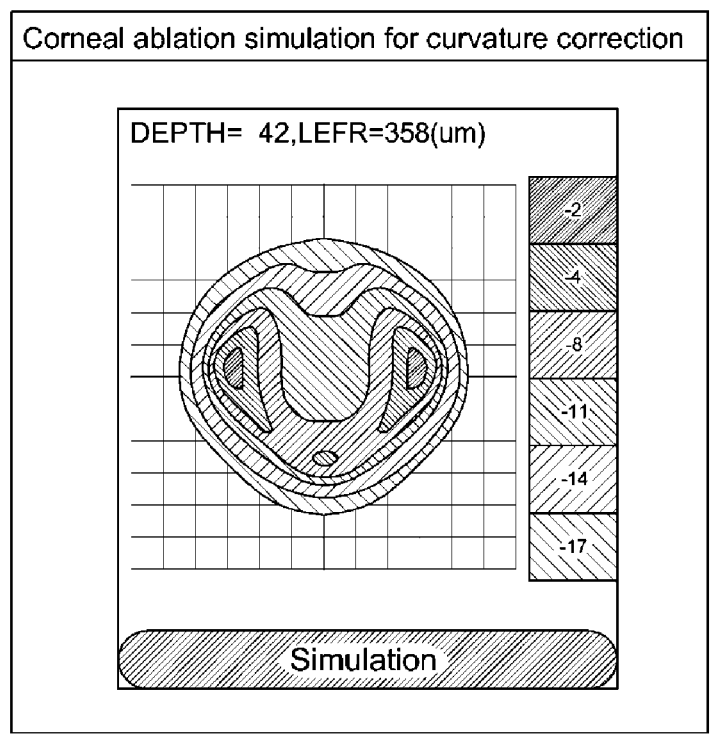

FIG. 27 shows a shape correction and curvature correction-integrated corneal ablation simulation, which is a corneal correction plan in which the shape correction and the curvature correction are integrated.

Three semi-cylinder astigmatic ablations are performed in three directions from upper, lower, left, and right directions, the cornea is cut by +1.5 D (for shape correction), respectively, and the cornea becomes Sph. −0.25 D, Cyl. −0.75 D Axis 180° (for curvature correction).

Figure 28:
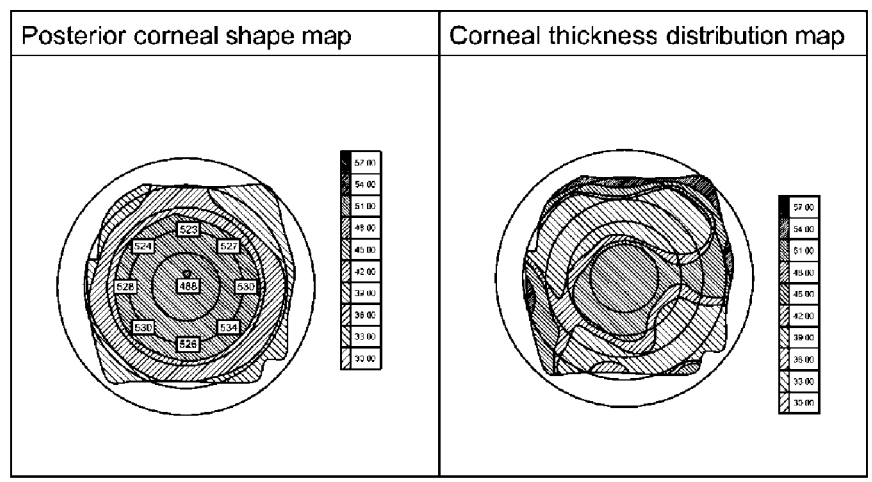

The postoperative results in this Example 1 are shown in FIG. 28.

FIG. 28 shows that the surgery is performed in Sph. −0.25 D, Cyl. −0.5 D Axis 100° (spherical equivalent=−0.5 D), and the unaided visual acuity in distance vision is increased to 1.0 while the unaided visual acuity in near vision is increased to 0.65.

Even though the corneal ablation is performed for the hyperopic correction of cutting the peripheral cornea by +1 D, the central thickness of the cornea is decreased from 515 μm to 488 μm, postoperatively. In addition, the posterior corneal cone is more concentrated in the central cornea than before surgery. Thus, distortion of the cornea caused by the intraocular pressure is prevented, thereby suppressing the generation of a high-order aberration.

EXAMPLE 2

Example 2 is a clinical case in which astigmatism is corrected through one semi-cylinder astigmatic ablation in one direction and the shape correction is performed through two semi-cylinder astigmatic ablations in two directions (1CD/1SA+2CD/2SA), which are substituted for the curvature (low-order aberration) correction, and the cornea is intentionally cut for curvature correction by +0.75 D in order to increase near vision.

Figure 29:
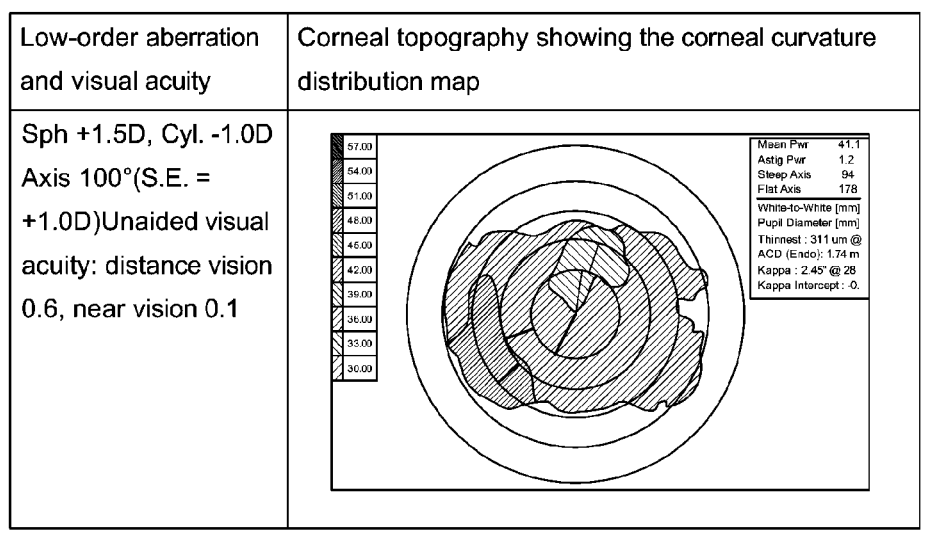

FIG. 29 shows the state of the cornea before ablation, and the low-order aberration and visual acuity of the eye to be corrected before surgery.

Figure 30:
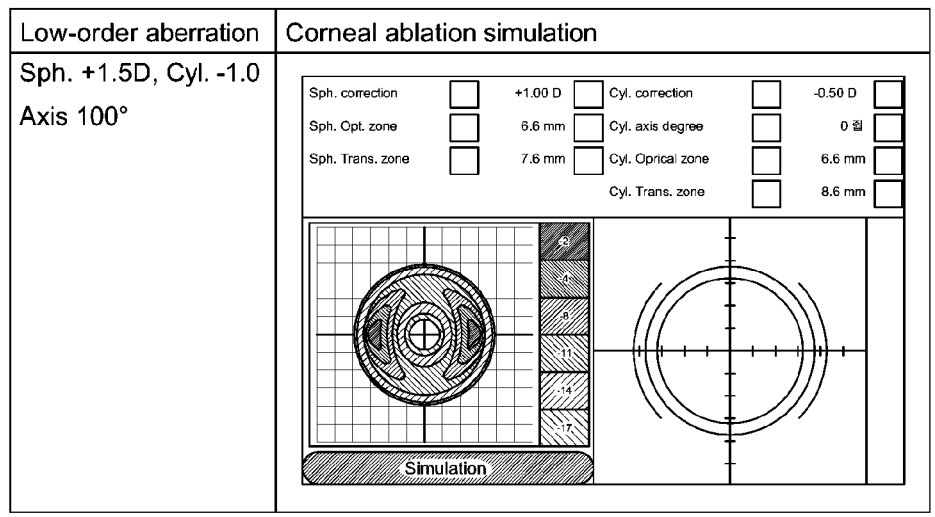

In this case, according to the conventional laser vision correction method, as shown in FIG. 30, a corneal curvature correction plan is applied, and the measured low-order aberration is directly inputted to the laser so as to perform corneal ablation.

Figure 31:
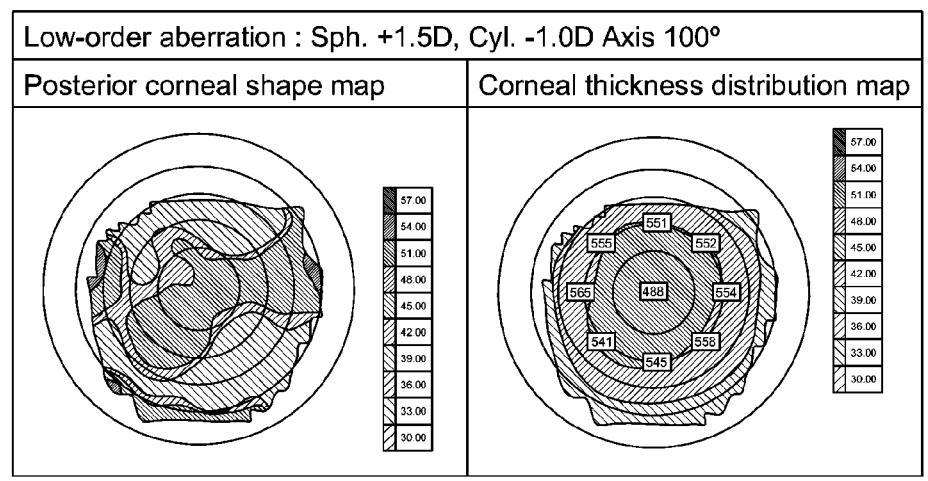

Meanwhile, as to explain an ablation method of performing the integrated correction on the corneal shape and curvature according to an embodiment of the present invention, as shown in FIG. 31, the necessary data of the cornea to be cut is collected by the information collection device.

If the low-order aberration is converted such that the astigmatism is represented by a positive value, Sph. +1.5 D, Cyl. −1.0 D Axis 100° is converted into Sph. +0.5 D, Cyl. +1.0 D Axis 10°.

In addition, an ablation plan can be created using the integrated corneal ablation program as follows.

1) The cornea symmetrically has astigmatism of +1.0 D on both sides about an axis of 10°. However, the upper thickness of the cornea is 605 μm and the lower thickness of the cornea is 565 μm, in which the thickness deviation is large. Therefore, the astigmatic ablation method of the existing curvature correction scheme is not performed, and one partial corneal ablation plan performed by +2 D in the direction of 10° is created and inputted for only the upper portion of the cornea to correct astigmatism while reducing the thickness deviation.

2) In addition, in order to concentrate the posterior corneal cone dispersed in the temporal direction of the eye to the center, two semi-cylinder astigmatic ablation plans performed by +1 D, respectively, in two directions including the upper and nasal directions are created and inputted.

3) When executing the two semi-cylinder astigmatic ablation plans that were created, the myopic spherical aberration to be generated is −0.5 D, and when the myopic spherical aberration is summed up with the inputted spherical aberration of the cornea of +0.5 D, the interlocked spherical aberration becomes 0 D. Therefore, it is unnecessary to perform the corneal ablation for correcting the spherical aberration interlocked with the laser.

4) In addition, if the near vision is desired to be increased after cutting the cornea, the operator may intentionally input hyperopic ablation of +0.75 D to modify or add the corneal ablation plan.

Figure 32:
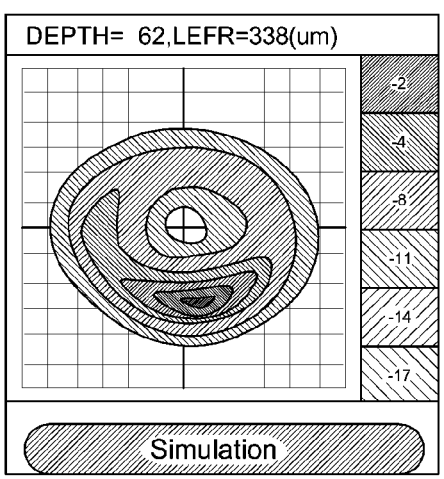

5) With these procedures, one semi-cylinder astigmatic ablation (1SA) and two semi-cylinder astigmatic ablations (2SA) and the corneal ablation for correcting the spherical aberration of Sph. +0.75 D are integrated to generate the simulation map, the corneal ablation simulation map as shown in FIG. 32 is created.

Figure 33:
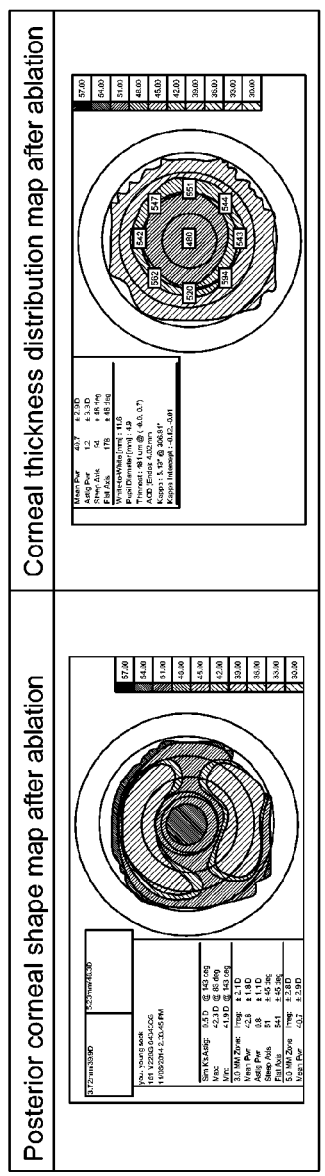

When the laser control unit of the laser equipment receives the integrated corneal ablation plan of the operation device 120 and performs the corneal ablation, the result as shown in FIG. 33 can be obtained.

In the result of the surgery shown in FIG. 33, the low-order aberration after ablation is Sph. −0.5 D, Cyl. −0.5 D Axis 180° (SE=−0.75 D), and the unaided visual acuity in distance vision is 0.7 while the unaided visual acuity in near vision is 0.8.

The results obtained by performing the integrated corneal ablation are summarized as follows.

Even though the corneal ablation was performed for the hyperopic correction, the intraocular pressure is concentrated at the central portion of the cornea. In addition, the posterior corneal cone came into the center, and the corneal distortion is corrected, thereby achieving the correction of the focal distance and the focal direction. Further, the symmetric corneal shape is maintained due to the concentration of the intraocular pressure at the central portion of the cornea after the cornea ablation, so that the possibility of the focus dispersion due to the defective shape and the vision deterioration due to the focus dispersion are remarkably reduced.

What is claimed is:

1. A corneal ablation system comprising:
    an operation device for collecting corneal status information that includes information of a low-order aberration of a cornea, a corneal thickness distribution map, and a posterior corneal shape map and creating an integrated corneal ablation plan for simultaneously correcting a defective shape and a curvature error of the cornea according to the corneal status information;
    a laser control unit for controlling a laser module according to the integrated corneal ablation plan transmitted from the operation device; and
    the laser module for generating and transmitting laser light to an optical unit under control of the laser control unit,
    wherein the operation device is configured to:
    create a partial corneal ablation plan for cutting the cornea on a region except for an eccentric posterior corneal cone by using the corneal thickness distribution map and the posterior corneal shape map to reduce thickness deviation from a point symmetry;
    estimate curvature fluctuation that is generated upon execution of the partial corneal ablation plan to obtain a myopic spherical aberration for offsetting the curvature fluctuation;
    add the myopic spherical aberration to the low-order aberration of the cornea to obtain an interlocking low-order aberration, and
    create the integrated corneal ablation plan by integrating the partial corneal ablation plan with the interlocking low-order aberration.

2. The corneal ablation system of claim 1, wherein the operation device is configured to determine an ablation shape and an ablation amount of the cornea according to the partial corneal ablation plan, determine a cutting shape and a cutting amount for correcting the interlocking low-order aberration, and create the integrated corneal ablation plan by using information of the ablation shape, the ablation amount, the cutting shape and the cutting amount.

3. The corneal ablation system of claim 2,
further comprising:
    an ophthalmic measurement equipment for measuring at least one of the curvature error of the cornea, the corneal shape map, and the corneal thickness distribution map; and
    a laser equipment for irradiating the cornea with laser light,
    wherein the operation device is installed in the ophthalmic measurement equipment,
    the laser module is installed in the laser equipment, and
    the laser equipment is configured to cut the cornea according to the integrated corneal ablation plan from the ophthalmic measurement equipment.

4. The corneal ablation system of claim 2,
further comprising:
    a laser equipment for irradiating the cornea with laser light,
    wherein the operation device is installed in the laser equipment, and
    the laser equipment includes a laser display unit for allowing a user to confirm a process of performing an operation for cutting the cornea according to the integrated corneal ablation plan and an ablation result.

5. The corneal ablation system of claim 2, wherein the partial corneal ablation plan has a semi-cylinder astigmatic correction form and uses one of: (1) a semi-cylinder form and (2) at least two semi-cylinder forms that overlap with each other and further uses a quarter form that is obtained by dividinq the semi-cylinder form in half.

6. The corneal ablation system of claim 2, wherein the partial corneal ablation plan has a semi-cylinder astigmatic correction form and uses two or three semi-cylinder forms,
    when the two semi-cylinder forms are used, the two semi-cylinder forms overlap with each other, and
    when the three semi-cylinder forms are used, a first one of the three semi-cylinder forms overlaps with both second and third ones of the three semi-cylinder forms, and an amount of ablation by the first semi-cylinder form is the same as an amount of ablation by both the second and third semi-cylinder forms.

* * * * *